United States Patent [19]

Curtis et al.

[11] Patent Number: 5,033,488
[45] Date of Patent: Jul. 23, 1991

[54] DENTAL FLOSS

[75] Inventors: John P. Curtis, Piscataway, N.J.; Jan-Joost Pabst, Barcelona, Spain; James H. Kemp, New Brunswick, N.J.

[73] Assignee: Colgate-Palmolive Co., Piscataway, N.J.

[21] Appl. No.: 282,962

[22] Filed: Dec. 2, 1988

Related U.S. Application Data

[63] Continuation-in-part of Ser. No. 174,757, Mar. 29, 1988, abandoned.

[51] Int. Cl.5 ............................................. A61C 15/00
[52] U.S. Cl. ..................................... 132/321; 424/50
[58] Field of Search .............. 132/321, 322, 323, 324, 132/325, 326, 327, 328, 329; 424/50

[56] References Cited

U.S. PATENT DOCUMENTS

| 3,538,230 | 11/1970 | Pader et al. | 424/50 |
| 3,943,949 | 3/1976 | Ashton et al. | 132/321 |
| 4,029,113 | 6/1977 | Guyton | 132/321 |
| 4,304,245 | 12/1981 | Lichfield | 132/321 |
| 4,414,990 | 11/1987 | Yost | 132/321 |
| 4,645,662 | 2/1987 | Nakashima et al. | 424/50 |
| 4,776,358 | 10/1988 | Lorch | 433/216 |

Primary Examiner—John J. Wilson
Attorney, Agent, or Firm—Michael J. McGreal; Robert L. Stone; Robert C. Sullivan

[57] ABSTRACT

Porous, high strength (that is, "Expanded") polytetrafluoroethylene (PTFE) dental floss is coated with microcrystalline wax. If desired, the floss may also incorporate one or more actives tartar control anti-caries antiplaque and/or antibacterial actives and/or dentally acceptable agents such as polishing and abrasive agents, coolants, flavorants and/or coagulants.

9 Claims, 3 Drawing Sheets

DENTAL FLOSS

This application is a Continuation-in-part of application Ser. No. 174,757, filed Mar. 29, 1988 now abandoned.

FIELD OF THE INVENTION

This invention relates to coated dental flosses.

BACKGROUND

Dental flosses have long been used to clean the teeth and the gum margin, for instance, in U.S. Pat. No. 3,800,812. In the past, certain medicinal ingredients have been bonded to or incorporated in the floss, e.g., fluoride to protect the tooth enamel from acid attack. Bactericides have also been used to counter periodontal disease.

However, the use of floss to clean the teeth-a process which is generally referred to herein as "flossing"—which is a very important technique recommended by dentists to prevent tooth and gum disease—often produces bleeding from the gums.

There have been numerous attempts in the art to provide superior dental flosses. For example, U.S. Pat. No. 3,830,246 discloses a floss of unspecified composition which is impregnated with a fluoride. No wax coating is disclosed. In U.S. Pat. No. 3,897,795 floss containing fluoride (with no wax coating) is disclosed. In U.S. Pat. No. 4,215,478 floss containing fluoride (with no wax coating) is described. U.S. Pat. No. 4,033,365 discloses a floss designed to retain flavorants over a long period of time through the use of non-wax polymeric coatings containing spray-dried flavor particles. The material constituting the floss is synthetic or natural, (but polytetraflouroethylene i.e. PTFE which, in it original form was developed by E. I. DuPont de Nemours & Co., Inc. (DuPont) and sold by that company under its Trademark Teflon, is not mentioned, nor are other types of PTFE which will be described herein).

In U.S. Pat. No. 3,771,536 floss containing fluoride with non-wax coating is described.

U.S. Pat. No. 3,943,949 discloses a floss-like material comprising a bundle of natural or synthetic fibers (but not PTFE) coated with various waxes, including microcrystalline wax, containing spray-dried flavor particles.

The prior art, as exemplified by the patents discussed above, make it clear that flossing is an extremely important adjunct to proper dental hygiene. Moreover, it is known that no floss on the market has received the degree of consumer acceptance to the degree which the dental profession would like. Indeed, in U.S. Pat. No. 3,913,596, stiff paper was proposed as a substitute for floss. The insufficient consumer acceptance—despite often repeated directions by dentists to use floss—may arise from the fact that prior art flosses frequently caused gingival bleeding and are generally uncomfortable or difficult to use. Those conditions may arise primarily from the relatively high coefficient of friction (COF) of such flosses.

Thus, because prior art flosses have such high COFs, consumers must use substantial force to pull them between the teeth or so-called "contact points". Unfortunately, the user does not know when the floss will, in fact, pass between the contact points. When this suddenly occurs, the user does not have time to release the great force being applied. This appears to cause the flosses to be pulled into the gum, causing cuts which bleed, sometimes profusely.

In order to solve this problem, it has been unexpectedly discovered that floss made of porous, high strength Expanded PTFE is extremely effective to provide hygienic tooth and gum care. Moreover, excellent effect is also provided when the floss is coated with microcrystalline wax (MCW). The MCW, surprisingly, adheres to the porous, high strength PTFE which without a coating has a very low COF(below 0.08); and when coated with MCW generally has a COF intermediate between prior art floss white and uncoated PTFE (at least 0.08 to that of commercial flosses, say to about 0.15); depending on additives which may be present, the COF may be somewhat higher say to about 0.25.. It is believed that the COF characteristics of MCW coated PTFE when reduced below about 0.15 may result from partial removal of MCW by contact at the contact points, rendering PTFE thereby exposed to slide more easily between teeth. It is also noteworthy that PTFE in its original form sold as Teflon did not have sufficient tensile strength to be effective as floss. When pulled or stretched, it would readily break. Accordingly, several major benefits accrue from the present invention. First, the tensile strength of Expanded PTFE, described below, is quite satisfactory for pressures associated with flossing; second, the COF of Expanded PTFE is generally much lower than that of existing flosses and tapes even when coated with MCW, so that the floss of this invention can pass smoothly through the very narrow spaces between the teeth, etc., and clean the teeth and gums without excessive bleeding; third, the MCW is an excellent carrier for a variety of actives and agents which promote oral hygiene even in those instances where the COF is at levels comparable to the prior art as will be described.

Thus, a primary object of this invention is to provide a floss for dental and gingival cleaning made of porous, high strength PTFE (that is Expanded PTFE) coated with MCW. An additional object is to incorporate on, below or in the MCW coating an active which promotes oral hygiene and/or other dentally acceptable agent.

Moreover, another object is to provide an Expanded PTFE floss adheringly coated with MCW which incorporates one or more coagulants which inhibit gingival bleeding, particularly in a situation where the presence of particular oral hygiene promoting actives may raise the COF, to thereby spare the user of the discomfort of the presence of blood in the oral cavity.

Materials promoting oral hygiene which may h=introduced on MCW coating of the floss include antiplaque, anti-caries, anti-bacterial and/or tartar control actives preferably—although not necessarily—in conjunction with coagulant.

A further object of this invention is to incorporate in the MCW coating of the floss other orally acceptable agents, such as coolants, flavorants, colorants, polishing and abrasive agents and the like.

THE FIGURES

Figure 4:
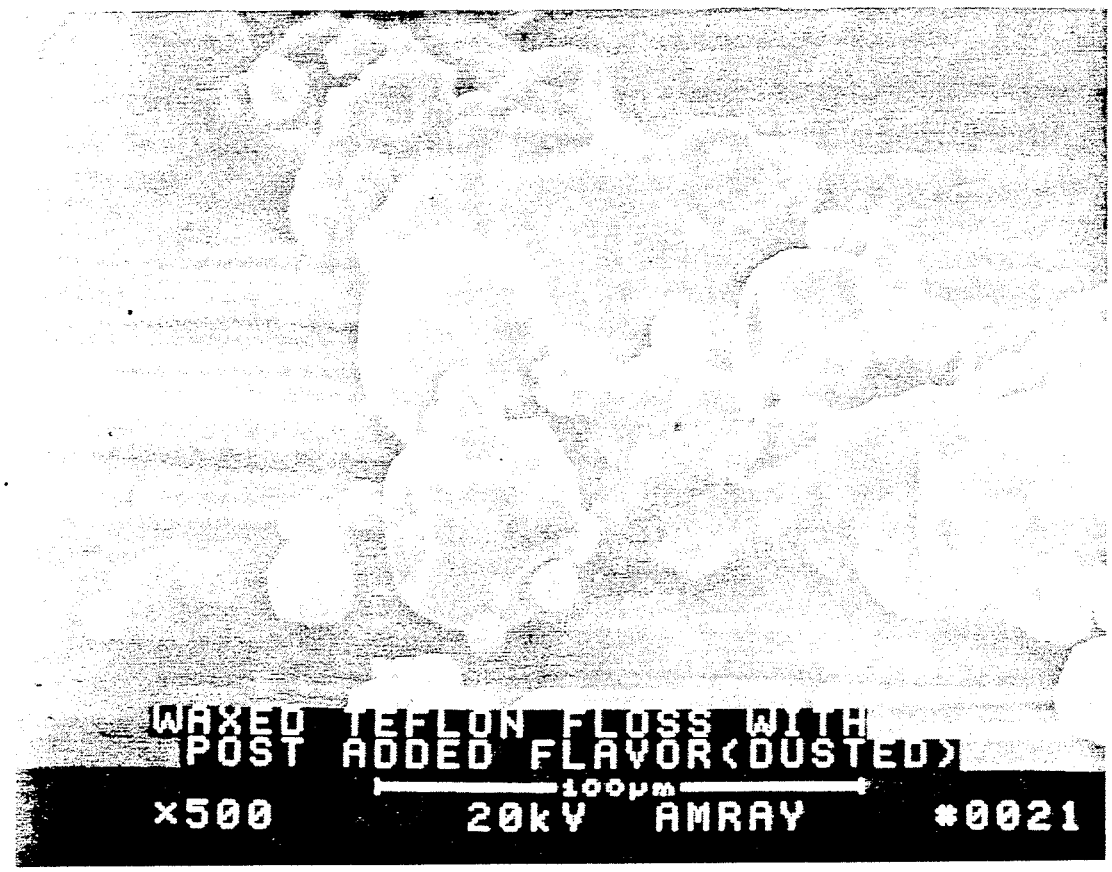
FIG. 4 is an SEM picture at 500 magnification showing particles of flavor post-added by dusting over an MCW coating on the surface of Expanded PTFE, both of which appear in the background.

As an alternative embodiment to FIG. 4, the flavor may be incorporated on the floss by adding spray dried flavor to the MCW and coating the mixture on the floss by immersing the floss in a bath of the mixture. As an additional alternative, the floss may be treated first by immersing it in a flavor bath and then post-coating with a bath of MCW.

As further alternatives to FIG. 4, flavor can be replaced or combined with actives such as anti-plaque, anti-caries and/or anti-tartar actives or other dentally acceptable agents.

DETAILED DESCRIPTION

The original PTFE developed by DuPont commercially as Teflon has a number of desirable physical properties, including great chemical and physical inertness. The latter property, commonly referred to as "non-stick", while of great advantage in some applications, made it very difficult to use the material in combination with other materials. Moreover, Teflon tended to quickly break or to rip when stretched or pulled with pressure, thus making it difficult to use as dental floss.

In more recent years, modified versons of PTFE have been developed, especially by W. L. Gore & Associates, Inc., Newark, Del. (hereinafter "Gore"). As well explained in Gore U.S. Pat. No. 3,953,566, incorporated herein by reference, this is attained by uni-axial or bi-axial stretching of the PTFE coupled with heating. Porosity is produced by the expansion. Such porous, high strength PTFE having such properties is also specifically referred to herein as "Expanded PTFE".

Figure 1:
FIG. 1 is a scanning electron microscopy (SEM) picture of the Expanded PTFE floss in virgin (uncoated) form at 1000 magnification, particularly showing the floss as being composed of a plurality of filaments. The projection on the right side of the picture is the outer surface of the floss which is separated from the interior to thereby expose the multi-filamentous nature of the interior.
Figure 2:
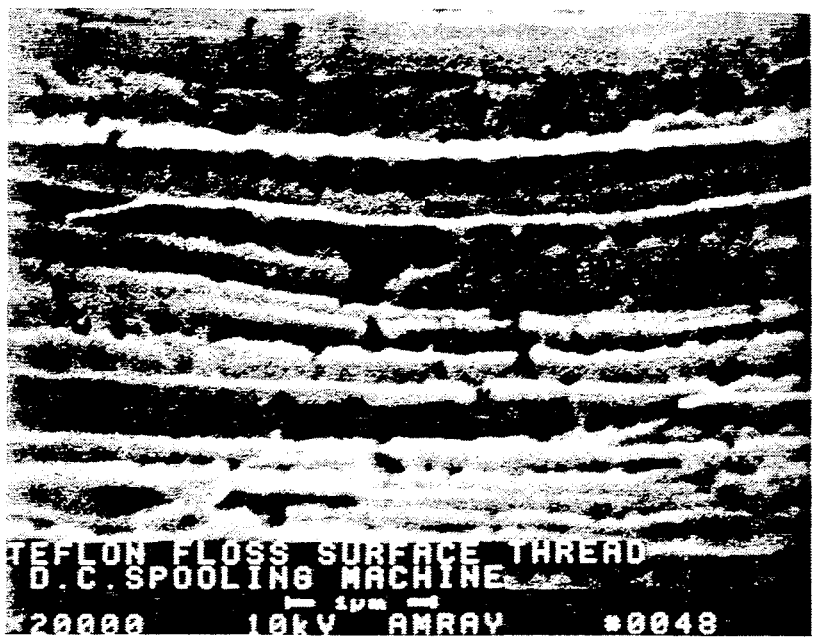
FIG. 2 is an SEM picture of a portion of the Expanded PTFE interior of FIG. 1 at 20000 magnification particularly showing the porous nature of the Expanded PTFE.
Figure 3:
FIG. 3 is an SEM picture of the Expanded PTFE surface having an MCW coating thereon at 500 magnification, particularly showing the non-continuous nature of the MCW coating, which is coated from an immersion bath onto the floss surface.

FIGS. 1 and 2 particularly depict such Expanded PTFE, with pores clearly visible in FIG. 2.

Expanded PTFE has a tensile strength of 10,000 psi 68,950 (kPa) and above, porosity of at least 90% and a polymeric matrix strength in excess of 100,000 psi (689,500 kPa). In contrast, conventional PTFE after sintering typically has a maximum tensile strength of about 3,000 psi (20,685 kPa) and for conventional extruded and calendered tape the maximum is about 5,000 psi (34,475 kPa).

Gore U.S. Pat. No. 3,962,153, incorporated herein by reference, discloses a further step in the manufacture of Expanded PTFE which involves stretching the PTFE at a high rate, i.e., above 2000% per second, below the melting point of the PTFE.

Gore U.S. Pat. Nos. 4,096,227 and 4,187,390, each incorporated here by references contain further information relating to the production and properties of expanded PTFE.

Such Expanded PTFEs are used in the present invention, especially those having the properties described in the above '566, '227, '390 and '153 patents.

Other Gore U.S. Patents of interest are 4,256,806; 4,385,093; and 4,478,665 which describe how various fillers such as carbon black, graphite, pigments, titanium dioxide, zirconium dioxide, asbestos, silica, potassium titanate and dielectric fluids such as polysiloxane may be incorporated into the PTFE, apparently to produce changes in bonding abilities to produce multi-layered articles.

Expanded PTFE, has a rather low COF (below 0.08) compared to COF in the vicinity of about 0.2 for prior art commercial floss. The present inventors discovered that, to their surprise, from amongst different waxes, microcrystalline wax (MCW) in particular adheres to Expanded PTFE and unexpectedly, results in at least two important benefits: First, the MCW provides a COF sufficiently high to permit the user to securely grasp the floss and tapes; but generally not so high as that of the prior art. Second, the MCW coating is capable of carrying a wide variety of actives and agents associated with oral care, that is oral hygiene promoting agent actives such as anti-plaque actives agent, anticaries actives and anti-tartar actives and dentally acceptable agents such as flavor, whitener, polishing agent and the like. Further, with many of such actives or agents the COF remains intermediate between the very low COF of Expanded PTFE (below 0.08) and the COF of commercial flosses, say about 0.08 to 0.15.

Numerous grades of MCW are available commercially, for instance from Petrolite, Corp. of Tulsa, Okla. and Boler Petroleum Company, Wayne, Pa. Such grades of wax are typically food grade materials. They are suitable for coating and adhering to expanded PTFE floss. A sampling of available grades from Petrolite Corp. and/or Boler Petroleum Company with physical properties is set forth in the following Table:

TABLE

| MICRO-CRYSTAL-LINE WAX | MELTING POINT °C. | ASTM D-1321 PENETRATION POINTS | | | |
|---|---|---|---|---|---|
| | | 25° C. | 37.8° C. | 93.3° C. | 60° C. |
| Ultraflex* | 65.6 | 29 | | 190 | |
| Bowax* 1018 | 68.3 | 26 | 70 | | |
| Victory* | 78.9 | 27 | | 125 | |
| Be Square* 175 | 83.9 | 17 | | 60 | |
| Starwax* | 85.6 | 14 | | 45 | |
| Be Square 185 | 87.8 | 9 | | 30 | |
| Be Square 195 | 92.2 | 6 | | | 65 |
| Petrolite* C-700 | 92.2 | 6 | | | 65 |
| Petrolite C-1035 | 93.3 | 5 | | | 55 |
| Mekon* White | 93.3 | 5 | | | 55 |
| Fortex* | 96.1 | 4 | | | 55 |

*Trademarks

Commercial waxes are mixtures of hydrocarbons. The molecular weights of different waxes are the average of the molecular weights of their hydrocarbon constituents. Although paraffin waxes which are mainly composed of normal acyclic hydrocarbons can frequently be characterized by their average molecular weights, it is more difficult to similarly characterize MCWs which typically substantial, but varying, amounts of secondary and tertiary acyclic hydrocarbon isomers and/or cyclic hydrocarbons. Thus, there is not necessarily a direct correlation between melting point and molecular weight of MCWs. Nevertheless, lower melting MCWs do generally have lower molecular weight and higher melting MCWs generally have higher molecular weights. For instance, Victory MCW, having a melting point of 78.9° C., has an average M.W. of about 650. The lower melting (65.6° C.) Ultraflex has an average M.W. of about 580 and the higher melting MCWs (about 82° C.) in the table above have average M.Ws. of above about 700 to 800 and higher.

Optimum adherence to expanded PTFE occurs with microcrystalline wax having a molecular weight of about 600–700 and a melting point of about 76°–80° C. An MCW grade such as that available from Petrolite, Corp. as Victory and an alternative MCW available from Witco as Witco* 445 are preferred. Witco 445 MCW has a melting point of 78.9° C. and similar penetration point characteristic to Victory MCW. Its average molecular weight is about 650.

As indicated, the MCW coated Expanded PTFE flosses of this invention may have incorporated thereon below, in or on the MCW coating one or more "active" or "agent".

The flosses of this invention may have incorporated thereon, for instance below, above or within (including encapsulated) their MCW coatings, one or more "active" or "agent". One type of agent may be a coagulant (or, "coagulating agent") to inhibit bleeding produced by flossing. Although the flosses of the present invention are less prone to cause bleeding; than typically occurs with many flosses of the prior art, some bleeding could occur. Particularly when the user has sensitive gingival tissue, it could be desirable to include a coagulant. Preferably, the coagulant is mixed in the MCW coating and may include K vitamins (1–4), calcium ions in the form of a soluble (water) calcium salt and blood factors that initiate the coagulation cascade. It is possible to incorporate other coagulants from solution in finely dispersed form in the MCW coating medium. Alternatively, the coagulants may be solubilized in non-toxic solvents, e.g., ethanol, polyethylene terephthlate, ether, etc. Further, the coagulating agents may be applied to the MCW coating during or after drying of the MCW.

In addition to the coagulants specified above, the following may be used in this invention: aminocaproic acid, tranexamic acid, adrenaline, alum, noradrenaline, iron salts, zinc salts and calcium alginate. Additional agents are described in Martindale (The Extra Pharmacopoeia), The Pharmaceutical Press, London, Ed. J. E. F. Reynolds.

It is desirable to get the coagulating agent(s) to the site of bleeding as quickly as possible. A preferred carrier for this purpose for incorporation within the MCW is a water soluble type of resin, such as PEG (polyethylene glycol) 6000 or 4000.

It is within the scope of this invention that the MCW coated Expanded PTFE flosses incorporate various actives against particular oral hygiene problems.

Thus, it may be desirable to incorporate the anticalculus agents of the type described in U.S. Pat. No. 4,627,977, of Colgate-Palmolive Company, the disclosure of which patent is incorporated herein by reference, and summarized in part below.

Based upon the '977 patent, it may be desirable to incorporate a tartar control active with the MCW coated Expanded PTFE floss. In this regard, a desirable active is pyrophosphate, preferably 3.3% pyrophosphate ion, NaF, preferably 0.2% and the polycarboxylate, Gantrez, preferably 1%. These percentages may vary, but, as noted in the '977 patent, the presence of fluoride ions tends to significantly inhibit the hydrolysis of the pyrophosphates by oral enzymes.

Other anti-tartar actives which may be incorporated in the MCW are zinc chloride and aluminum salts.

With regard to the extent to which the tartar control actives actually release the agents, a test using another type of floss incorporating pyrophosphate with ten subjects has demonstrated that at least 12% of the agent was released (in the poorest case) up to 83% (in the best case). Such a test may have a wide variation, probably reflecting the different efficiencies the panelists used in flossing. In any event, it appears that a substantial amount of the aforesaid anti-tartar active is released into the subgingival regions during flossing—and that such is release is very important to tartar control.

It appears that an optiminum modality to ensure release of pyrophosphates incorporated in the coated floss of this invention is to utilize Gantrez (and its equivalents) since of the three enzymes that cause the degration of the pyrophosphate, the NaF inhibits one and Gantrez inhibits the other two.

As noted above, it is also desirable in many cases, to incorporate various antibiotic anti-plaque actives in the floss either alone or in conjunction with coagulant and/or tartar control active described. Additionally, there may be incorporated anti-caries actives, e.g., sodium monofluorophosphate, sodium fluoride or stannous fluoride.

There is literature relating to the subject of the use of actives in connection with the control of periodontal disease (PD), for example, the article by J. M. Goodson et al. entitled "Tetracycline-containing Fibers for Controlled Delivery to Periodontal Pockets", Journal Periodontal, Vol. 54 (10), pages 575–579, October 1983. However, while this and many other references acknowledge the general utility of antibiotics which may be anti-plaque additives in controlling PD, they lack specific teachings relating to the mode of ensuring that such medicines actually reach the periodontal pockets where PD originates and grows.

Thus, the present invention, in teaching that the antibacterial agents (ABAs), such as tetracycline, can be most effectively employed by incorporating them in conjunction with a MCW coating on the Expanded PTFE floss of this invention, particularly in an MCW coating thereon, is a significant advance in the art.

If desired, dentally acceptable agents such as a cooling agent, e.g. menthol and anologues such as N-ether-p-methane-3-carboxamide may be incorporated with the coated floss to help the patient to detect where the treatment has been applied.

It may also be very useful to incorporate colorant agents or fluorescent agents to identify residual plaque deposits such as FD&C Red 3, FD&C Red 4, for example.

Actives which may be applied or otherwise incorporated with the coated floss which promote oral hygiene, include fluoride, cetylpyridinium chloride, benzethonium chloride (and other quaternary salts), chlorhexidine, hexachlorophene soluble pyrophosphate salts with hydrolysis inhibiting agent(s). Compounds that assist in wound healing such as allantoin, zinc sulphate and similar astringents may also be present.

The agents preferably are incorporated in the MCW used to coat flosses but they may be embedded within the floss filament prior to coating or dusted on after coating, for example. It may be desirable, for example, to immerse or coat the filaments of floss with the actives or agents before coating with MCW, while coating or after coating.

By way of further explanation, for example, that quaternary salts such as cetyl pyridinium chloride and benzethonium chloride, chlorhexidine, etc., may leach or permeate slowly from the interior of the filaments through an MCW coating and then into the oral cavity. Further, polishing agents such as hydrated amorphous silica, hydrated alumina, calcium carbonate and so forth may be mixed with the Expanded PTFE during formation.

A surprising and unexpected aspect of the present invention is that the particular wax, MCW, does in fact, "stick" (adhere) to the Expanded PTFE floss filament. Moreover, since the actives and agents described herein can be readily incorporated with the MCW coated Expanded PTFE itself a new family of dental flosses has been unexpectedly discovered.

A great advantage of the present invention is based on the generally low COF of MCW coated Expanded PTFE which can still be handled as a floss. Further the MCW coating gives it generally a COF intermediate between uncoated MCW Expanded PTFE floss and commercial floss and which is satisfactory for flossing, that is, about 0.08 to about 0.15.

The generally low COF of the MCW coated Expanded PTFE flosses of this invention gives them a significantly enhanced ability to glide easily between tight interproximal contact point areas and is gentler on gingival tissue, enamel, dentin and cementum then currently available commercial flosses. The MCW generally appears to be easily debrided from the floss at interproximal dental contact points so that the remaining exposed Expanded PTFE floss slides without tending to cause substantial gingival bleeding. Moreover, the Expanded PTFE is about as strong as conventional flosses but it is significantly more resistant to shredding and breaking. Indeed, its filaments tend not to readily unravel.

The key property—COF—can be observed by the following example which set forth test results of the COF of the flosses of the present invention compared to leading brands of commercial dental floss now on the U.S. market and to Expanded PTFE floss having no MCW coating.

EXAMPLE

FLOSS COEFFICIENTS OF FRICTION (COFs)

Comparative Samples

| COMMERCIAL FLOSS | | EXPANDED PTFE FLOSS WITHOUT MCW | |
|---|---|---|---|
| | COF | | COF |
| A. Waxed (I) | 0.22930 | A'— Virgin (Expanded PTPE) | 0.06886 |
| B. Unwaxed | 0.21214 | | |
| C. Extrafine | 0.20098 | B'— Virgin with 2% TiO$_2$ | 0.07152 |
| D. Waxed (II) | 0.15820 | C'— Virgin with 8% TiO$_2$ | 0.07926 |
| | | D'— Virgin with Anti-Tartar Active | 0.17455 |

| Present Invention (Expanded PTFE Floss With MCW Coating) | COF |
|---|---|
| 1. MCW coated Expanded PTFE with 8% TiO$_2$ and white oil | 0.08970 |
| 2. MCW coated Expanded PTFE with flavorant agent | 0.09148 |
| 3. MCW Coated Expanded PTFE | 0.10352 |
| 4. MCW coated Expanded PTFE with flavorant agent | 0.18080 |
| 5. MCW coated Expanded PTFE with anti-tartar agent | 0.21605 |

The MCW employed in Nos. 1–5, above, is available from Petrolite, Corp. as "Victory" or "Victory White". The above data establishes that certain preferred embodiments of this invention have COFs substantially lower than any of the commercial flosses of the Comparative Samples, which is of significance since the latter are among the leading flosses now sold in the U.S. Moreover, the data shows that embodiments with MCW coating present COFs generally higher than unwaxed Expanded PTFE but generally lower than the commercial samples (unless special actives are present). Anti-tartar active does appear to raise the COF, but not to a level above that of commercial floss. It may be that with such active material, the PTFE is not readily exposed as the floss passes between an interdental contact point. In such situations it may be desirable to also include a coagulant.

The technique by which the COF is measured is based upon the technique described by Scott & Robbins, J. Soc. Cosmet. Chem., 31, Pages 179–200 (July/August, 1980). This technique, described for measuring friction of reference surfaces by particularly passing hair fibers through an immersed combing device and measuring the COF with Instron* Tensile Tester is suitable for COF measurement of dental floss with interstitial dental surfaces replacing the combing device. It is not necessary to immerse the dental surfaces.

A prime advantage of this invention is summarized as follows: Dental flosses have long been used to remove particles and other debris by debriding action. However, the use of these modalities has not been as high as desirable, in part due to the perception that flosses do not provide substantial additional oral care effectiveness—and because they are difficult to use and they often cause bleeding.

The present invention, however, encourages much greater use of the floss, including when combined with the actives and agents described because the user will obtain multiple benefits from not only the gentle cleaning action (the gentleness resulting from the generally low COF of the PTFE coated with MCW), but also from the action of the actives and agents. In addition, flossing is especially effective in the sub-gingival areas and thus can be effective to reduce sub-gingival plaque and root caries, especially when fluoride or another anti-caries active is employed. Moreover, use of coagulants to reduce bleeding—which often occurs with present flosses—will reduce the inhibition to use floss arising from bleeding—and thus encourage more regular flossing.

We claim:

1. A dental cleaning floss wherein said floss is comprised of expanded polytetrafluoroethylene having a tensile strength of at least 68,950 kPa, or polymeric matrix strength of at least 689,000 kPa and a coefficient of friction of at least about 0.08, said coefficient of friction having been increased from untreated polytetrafluoroethylene by having adhered to the surface of said polytetrafluoroethylene a microcrystalline wax having a molecular weight of about 580 to 800.

2. The floss of claim 1 wherein said floss has a coefficient of friction of about 0.08 to about 0.25.

3. The floss of claim 1 wherein the device incorporates at least one active material selected from the group consisting of anti-tartar active, anti-caries active, and anti-plaque active.

4. The floss of claim 3 wherein a coagulating agent is also present and is selected from the group comprising: K vitamins (1-4), calcium ions in the form a water soluble calcium salt, blood factors that initiate the coagulation cascade, aminocoproic acid, tranexamic acid, adrelaline, alum, noradreline, iron salts and calcium alginate.

5. The floss of claim 3 wherein anti-tartar active is present and comprises a pyrophosphate and sodium fluoride.

6. The floss of claim 3 wherein anti-tartar active is present and is selected from the group comprising zinc chloride, tetrasodium pyrophosphate, sodium acid pyrophosphate and tetrapotassium pyrophosphate.

7. The floss of claim 3 wherein anti-caries active is present and is selected from the group comprising sodium monofluorophosphate, sodium fluoride and stannous fluoride.

8. The floss of claim 3 wherein anti-plaque active is present and is selected from the group comprising chlorhexidine, hexachlorophene, cetylpyridinium chloride and benzethonium chloride.

9. The floss of claim 1 wherein said microcrystalline wax has a melting point of about 76°-80° C.

* * * * *